United States Patent
Kandori et al.

(10) Patent No.: US 7,372,278 B2
(45) Date of Patent: May 13, 2008

(54) ELECTRIC POTENTIAL MEASURING APPARATUS ELECTROSTATIC CAPACITANCE MEASURING APPARATUS, ELECTRIC POTENTIAL MEASURING METHOD, ELECTROSTATIC CAPACITANCE MEASURING METHOD, AND IMAGE FORMING APPARATUS

(75) Inventors: Atsushi Kandori, Ebina (JP);
Yoshikatsu Ichimura, Tokyo (JP);
Takashi Ushijima, Yokohama (JP);
Yoshitaka Zaitsu, Kawasaki (JP);
Kaoru Noguchi, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 11/500,926

(22) Filed: Aug. 9, 2006

(65) Prior Publication Data
US 2007/0065169 A1 Mar. 22, 2007

(30) Foreign Application Priority Data
Aug. 16, 2005 (JP) .............................. 2005-235586

(51) Int. Cl.
*G01R 29/12* (2006.01)
*G03G 15/00* (2006.01)
(52) U.S. Cl. ........................................ 324/458; 399/48
(58) Field of Classification Search ................ 324/458, 324/457, 72, 661, 686, 452, 663, 109, 72.5; 73/658; 399/48, 73
See application file for complete search history.

(56) References Cited

U.S. PATENT DOCUMENTS

| | | | |
|---|---|---|---|
| 3,852,667 A | 12/1974 | Williams et al. ............... 324/72 |
| 3,997,839 A * | 12/1976 | Dreyfus et al. ............. 324/109 |
| 4,064,539 A * | 12/1977 | Lewiner et al. .......... 369/53.41 |
| 4,205,267 A | 5/1980 | Williams ..................... 324/458 |
| 4,720,682 A | 1/1988 | Ikushima et al. ........... 324/458 |
| 4,763,078 A | 8/1988 | Williams ..................... 324/458 |
| 4,835,461 A | 5/1989 | Snelling ..................... 324/109 |
| 5,212,451 A | 5/1993 | Werner, Jr. ................. 324/458 |
| 5,600,251 A * | 2/1997 | Akiyama ..................... 324/613 |
| 5,986,456 A * | 11/1999 | Yamashita ................... 324/457 |

(Continued)

FOREIGN PATENT DOCUMENTS

JP 2001-305471 10/2001

OTHER PUBLICATIONS

U.S. Appl. No. 10/550,450, filed Sep. 26, 2005, Yoshikatsu Ichimura et al, pending.
U.S. Appl. No. 10/540,978, filed Jun. 27, 2005, Yoshikatsu Ichimura et a, pending.
U.S. Appl. No. 10/551,112, filed Sep. 28, 2005, Susumu Yasuda et al, pending.
U.S. Appl. No. 10/798,315, filed Mar. 12, 2004, Susumu Yasuda et al, pending.

*Primary Examiner*—Andrew H Hirshfeld
*Assistant Examiner*—Hoai-an D Nguyen
(74) *Attorney, Agent, or Firm*—Fitzpatrick, Cella, Harper & Scinto

(57) ABSTRACT

An electric potential measuring apparatus includes a detecting electrode, a modulator for changing an electrostatic capacitance between a measurement object and the detecting electrode by mechanical vibration, a charge detector for detecting the amount of charges electrostatically induced in the detecting electrode by the modulator, and a vibration generating-detecting unit for selectively performing either a vibration generating function of exciting the mechanical vibration, or a detecting function of detecting the condition of the mechanical vibration.

18 Claims, 13 Drawing Sheets

U.S. PATENT DOCUMENTS

| | | | |
|---|---|---|---|
| 6,316,942 B1* | 11/2001 | Horiguchi | 324/457 |
| 6,573,725 B2* | 6/2003 | Kieres et al. | 324/458 |
| 7,149,442 B2* | 12/2006 | Ushijima et al. | 399/48 |
| 2003/0169428 A1* | 9/2003 | Lange | 356/464 |
| 2005/0030679 A1* | 2/2005 | Yakabe | 361/18 |
| 2006/0171728 A1* | 8/2006 | Ichimura et al. | 399/48 |

* cited by examiner

ELECTRIC POTENTIAL MEASURING APPARATUS ELECTROSTATIC CAPACITANCE MEASURING APPARATUS, ELECTRIC POTENTIAL MEASURING METHOD, ELECTROSTATIC CAPACITANCE MEASURING METHOD, AND IMAGE FORMING APPARATUS

BACKGROUND OF THE INVENTION

1. Field of the Invention

The present invention relates to an electric potential measuring apparatus, an image forming apparatus using the electric potential measuring apparatus, an electric potential measuring method, an electrostatic capacitance measuring apparatus, and an electrostatic capacitance measuring method.

2. Description of the Related Background Art

Conventionally, there exists an image forming apparatus that includes a photosensitive body and forms an image in an electrophotographic manner. In such an image forming apparatus, to form a high-quality image, the apparatus needs to be controlled while the electric potential of the photosensitive body is measured. To achieve the above-stated purpose, there has been proposed an example of the electric potential measuring apparatus in which a detecting electrode is located close to an electrically-charged photosensitive body (an object being measured, or a measurement object), the capacitance between the photosensitive body and the detecting electrode is mechanically changed as below-described, and a small amount of charges electrostatically induced in the detecting electrode is measured.

FIG. 12 shows a conceptual structure of an electric potential measuring apparatus. As illustrated in FIG. 12, a measurement object 501, a detecting electrode 502, and a charge detector 503 are arranged. In FIG. 12, reference character VD designates a surface electric potential of the measurement object 501. Reference character C1 designates a capacitance to be changed by a capacitance changing unit (a capacitance modulator) for changing the electrostatic capacitance between the photosensitive body 501 and the detecting electrode 502. Reference character VOUT designates a signal output from the charge detector 503.

As a method of mechanically changing the capacitance C1, there have been proposed a method in which the number of electric lines of force reaching the detecting electrode 502 from the measurement object 501 is periodically changed, and a method in which the detecting electrode 502 are periodically displaced.

U.S. Pat. No. 4,720,682 discloses a structure in which a fork-shaped shutter is interposed between a measurement object (a photosensitive body) and a detecting electrode, and the shutter is periodically moved in directions parallel with a surface of the measurement object such that electric field lines of force from the measurement object are periodically prevented from reaching the detecting electrode. The effective area of the detecting electrode viewed from the measurement object is thus changed, and the electrostatic capacitance between the measurement object and the detecting electrode is hence varied so that the electric potential of the measurement object can be detected.

Further, there has been proposed a structure in which a metal shielding member with an opening is arranged facing a measurement object, and a detecting electrode is disposed on an end portion of a fork-shaped vibrating member. U.S. Pat. No. 3,852,667 discloses a structure in which the detecting electrode is moved in a parallel manner right under the opening of the vibrating member, and the number of electric lines of force reaching the detecting electrode is accordingly changed so that the electrostatic capacitance is modulated.

U.S. Pat. No. 4,763,078 discloses a structure in which a detecting electrode is arranged on an end portion of a vibrator in the form of a cantilever that is vibrated to change the distance between a measurement object and the detecting electrode, and the electrostatic capacitance is thus modulated.

In the above-described electric potential measuring apparatuses, or electrostatic capacitance measuring apparatuses, the condition of the vibration for modulating the electrostatic capacitance must be detected to achieve a stabilized vibration of the fork-shaped shutter, or the vibrator. However, a sensor for detecting the vibration needs to be additionally arranged to detect the condition of the vibration, leading to an increase in the number of constituent components.

SUMMARY OF THE INVENTION

The present invention is directed to an electric potential measuring apparatus or method capable of detecting the condition of the vibration without using an additional sensor for detecting the condition of the vibration, and an image forming apparatus including the electric potential measuring apparatus.

According to one aspect of the present invention, there is provided an electric potential measuring apparatus which includes a detecting electrode, a modulator for changing an electrostatic capacitance between a measurement object and the detecting electrode by mechanical vibration, a charge detector for detecting an amount of charges electrostatically induced in the detecting electrode by the modulator, a vibration generator for exciting or generating the mechanical vibration, and a detector for detecting a condition of the mechanical vibration from the condition of the vibration generator. In the electric potential measuring apparatus, one of the excitement of the mechanical vibration and the detection of the condition of the mechanical vibration is selectively performed.

According to another aspect of the present invention, there is provided an electric potential measuring method which includes a step of changing an electrostatic capacitance between a measurement object and a detecting electrode by mechanical vibration, a step of detecting an amount of charges electrostatically induced in the detecting electrode in the changing step, and a step of measuring the electric potential of the measurement object based on the result obtained in the detecting step. In the electric potential measuring method, a condition of the mechanical vibration is detected, a manner of the excitement of the mechanical vibration is controlled based on a result of the detection of the condition of the mechanical vibration, and a period for exciting the mechanical vibration and a period for detecting the condition of the mechanical vibration are set so that those periods do not overlap with each other.

According to still another aspect of the present invention, there is provided an electrostatic capacitance measuring apparatus which includes a detecting electrode, a modulator for changing an electrostatic capacitance between a measurement object and the detecting electrode by mechanical vibration, a charge detector for detecting an amount of charges electrostatically induced in the detecting electrode by the modulator, a vibration generator for exciting or generating the mechanical vibration, and a detector for detecting a condition of the mechanical vibration from the condition of the vibration generator. In the electrostatic capacitance measuring apparatus, one of the excitement of the mechanical vibration and the detection of the condition of the mechanical vibration is selectively performed.

According to still another aspect of the present invention, there is provided an electrostatic capacitance measuring method which includes a step of changing an electrostatic capacitance between a measurement object and a detecting electrode by mechanical vibration, a step of detecting an amount of charges electrostatically induced in the detecting electrode in the changing step, and a step of measuring the electrostatic capacitance between the measurement object and the detecting electrode based on the result obtained in the detecting step. In the electrostatic capacitance measuring method, the condition of the mechanical vibration is detected, a manner of the excitement of the mechanical vibration is controlled based on the result of the detection of the condition of the mechanical vibration, and a period for exciting the mechanical vibration and a period for detecting the condition of the mechanical vibration are set so that those periods do not overlap with each other.

More specifically, two periods are established in an operation period of the apparatus. One is a period in which a driving signal for exciting or generating the vibration is supplied to a vibration generating-detecting unit. The other is a period in which a signal generated by the vibration is detected by the vibration generating-detecting unit while no driving signal is supplied to the vibration generating-detecting unit. Accordingly, generation of the vibration and detection of the vibration can be achieved by using a single constituent unit of the vibration generating-detecting unit.

According to yet still another aspect of the present invention, there is provided an image forming apparatus which includes the above-described electric potential measuring apparatus of the present invention, and an image forming unit. In the image forming apparatus, a surface of the detecting electrode in the electric potential measuring apparatus is disposed facing an object surface being measured in the image forming unit, and the image forming unit controls conditions of image formation based on the result of a signal detected by the electric potential measuring apparatus.

The features of the present invention will be more readily understood in connection with the following detailed description of the embodiments and examples of the invention in connection with the drawings.

DESCRIPTION OF THE EMBODIMENTS

Embodiments of an electric potential or electrostatic capacitance measuring apparatus or method, and an image forming apparatus of the present invention will hereinafter be described with reference to the drawings. In an electrostatic capacitance measuring apparatus or method of the present invention, an electric potential, a change in the distance between a measurement object and an electrode, a change in the dielectric constant of a portion between a measurement object and an electrode, or the like is measured by detection of a change in the electrostatic capacitance.

A first embodiment directed to an electric potential measuring apparatus will be described with reference to FIGS. 1, 2, and 3A to 3C. In the first embodiment, a modulator changes the electrostatic capacitance between a surface of a measurement object and a detecting electrode by mechanical vibration. Electrical charges are electrostatically induced in the detecting electrode by the modulator, and the amount of the thus-induced charges is detected. The apparatus further includes a vibration generating-detecting unit that selectively executes the following two functions. One is a function of exciting the mechanical vibration, and the other is a function of detecting the condition of the mechanical vibration. The mechanical vibration is the vibrating motion of a vibrator that constitutes the modulator, for example.

Figure 1:
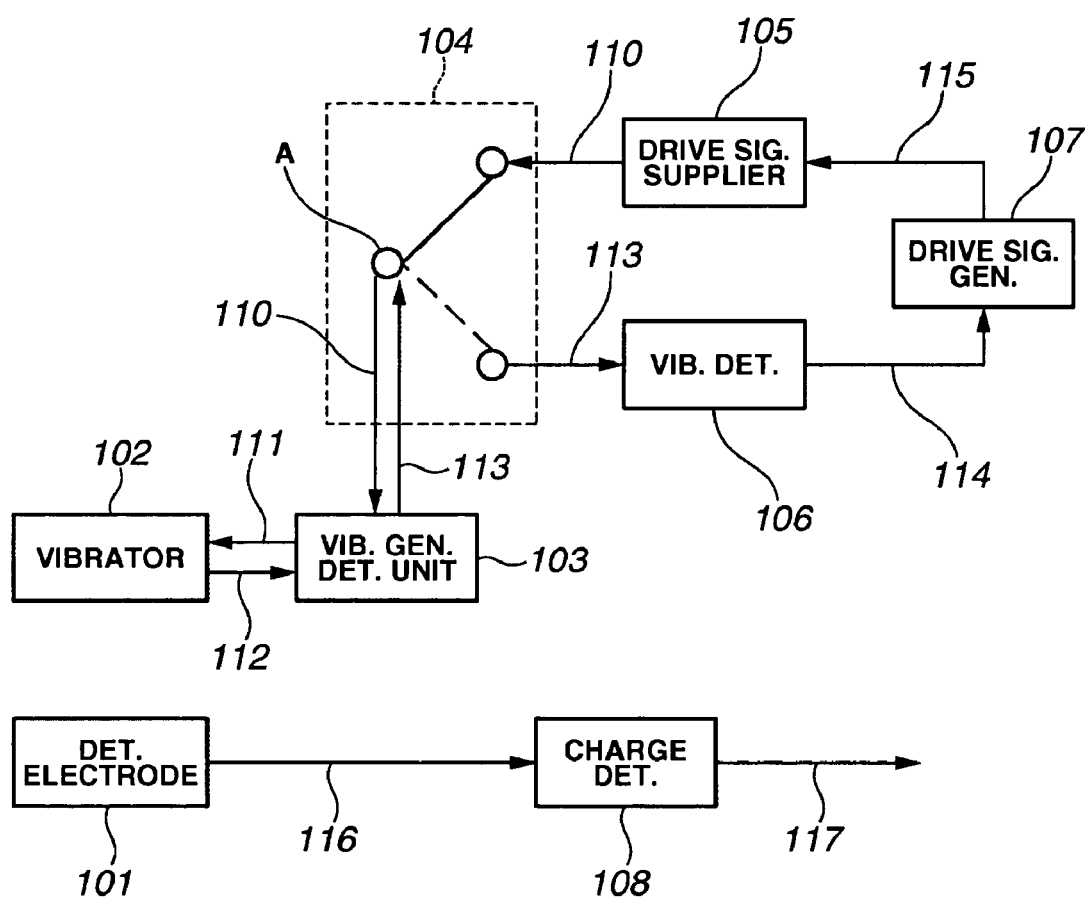
FIG. 1 is a block diagram illustrating an electric potential measuring apparatus of a first embodiment according to the present invention.

As illustrated in FIG. 1, the apparatus of the first embodiment includes the detecting electrode 101, and the vibrator 102. As the vibration generating-detecting unit 103 (the vibration generator), there is also arranged an electromechanical converting unit 103 that excites the vibration of the vibrator 102, and detects the condition of the vibration of the vibrator 102. Here, the electromechanical converting unit includes not only a unit for converting electric energy into mechanical energy, but also a unit for converting mechanical energy into electric energy. An example of the electromechanical converting unit is a piezoelectric device.

In the apparatus, there are further arranged a wiring changing unit 104, such as a switch, a driving signal supplier 105, such as a driving circuit for generating a driving signal for driving the vibrator 102, a vibration detector 106, such as a detecting circuit for detecting the condition of the vibration of the vibrator 102, and a driving signal generator 107, such as an oscillator for generating a signal with a reference frequency for generating the driving signal. Those units can be considered to constitute a portion of the vibration generating-detecting unit.

Furthermore, a charge detector 108 is disposed in the apparatus. The charge detector 108 detects the amount of charges electrostatically induced in the detecting electrode 101.

The vibrator 102 (the modulator) serves as a chopper for periodically occluding electric lines of force reaching the detecting electrode 101 from a measurement object (e.g., a photosensitive drum) that is not shown in FIG. 1. A piezoelectric unit, serving as the vibration generator, which will be described later, is disposed on the vibrator 102 to generate the vibration of the vibrator 102.

Figure 2:
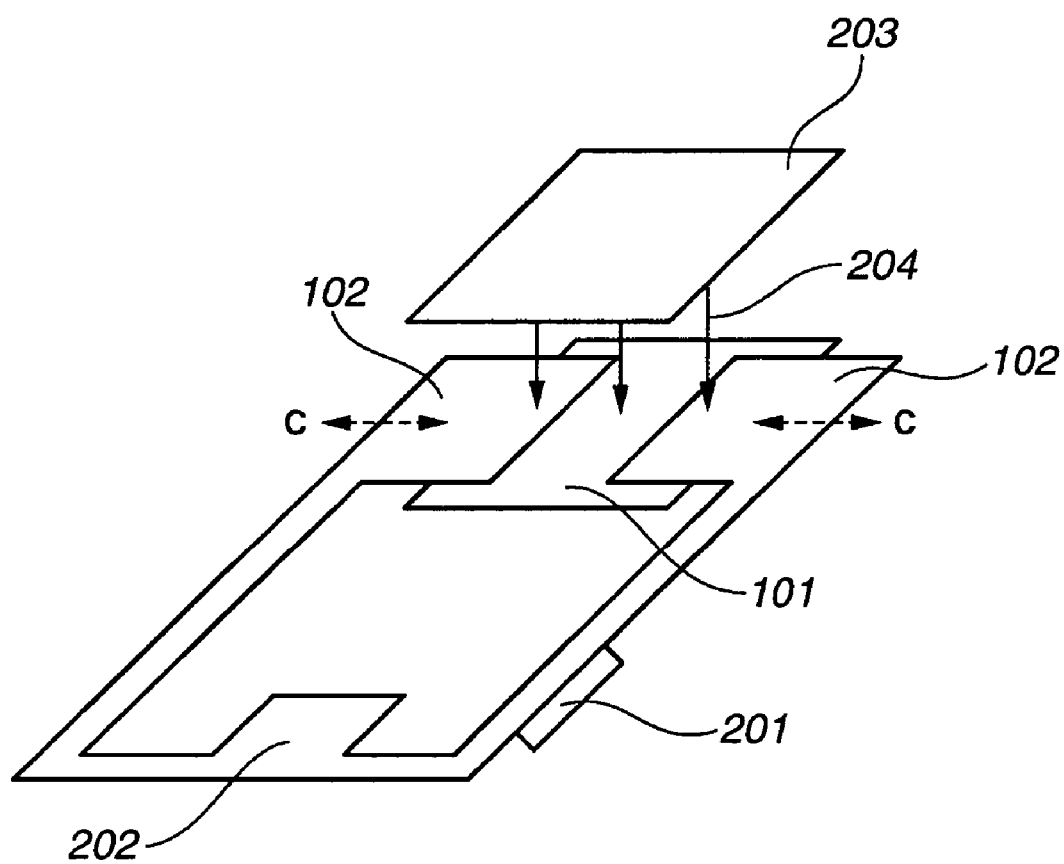
FIG. 2 is a schematic perspective view illustrating a vibration generating-detecting unit in the first embodiment.

FIG. 2 illustrates an example of the vibrator 102 in the first embodiment. In FIG. 2, reference numeral 201 designates a piezoelectric device. Reference numeral 202 designates a fixed end portion of the vibrator 102. Reference numeral 203 designates a measurement surface (a surface of the measurement object). Reference numeral 204 designates electric field lines of force reaching the detecting electrode 101 from the measurement surface 203.

Figure 3A:
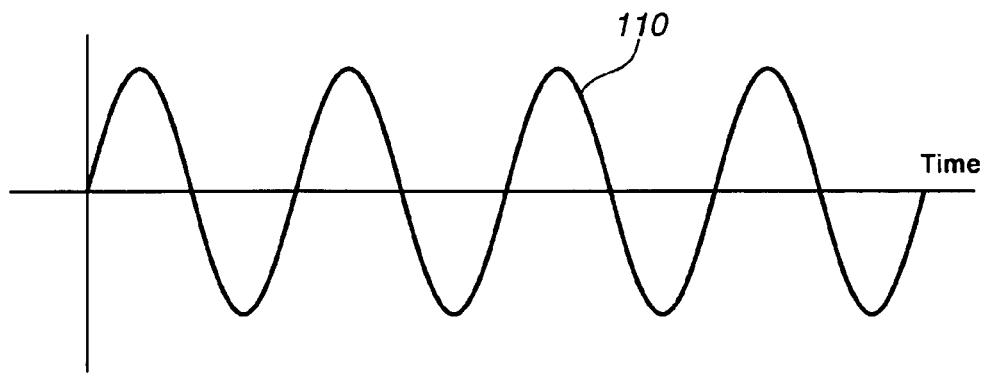
FIGS. 3A to 3C are graphs showing signals appearing in the first embodiment.
Figure 3B:
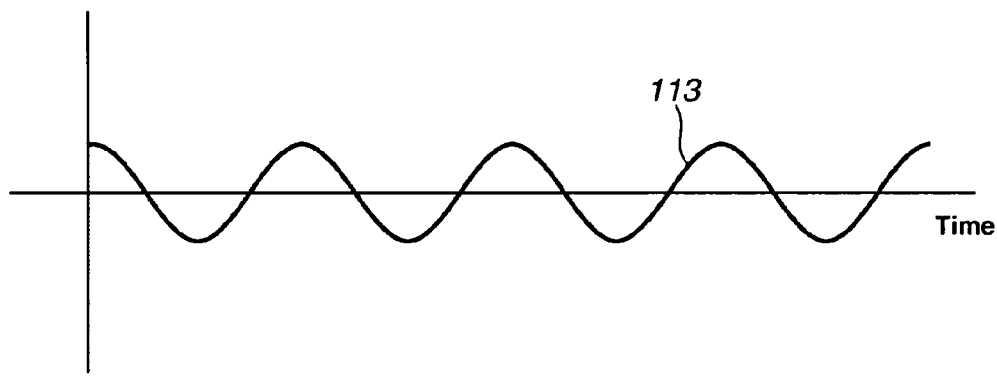
Figure 3C:
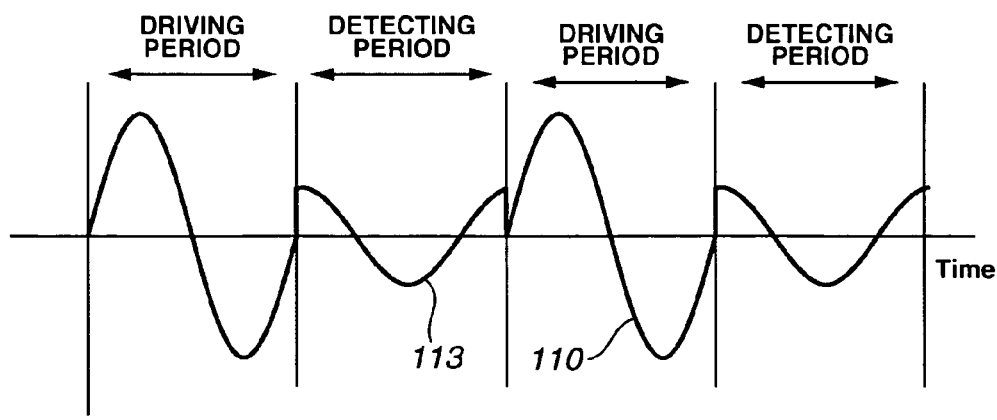

FIGS. 3A to 3C show signals appearing in the first embodiment. In those graphs, the abscissa indicates time, and the ordinate indicates the magnitude of the signal. FIG. 3A shows a driving signal 110 supplied from the driving signal supplier 105. An analog signal is shown here, but a digital signal, such as pulsed signals, can also be used as the driving signal.

FIG. 3B shows a vibration signal (a detection signal) 113 generated from the piezoelectric device 201 due to vibration 112 of the vibrator 102. A waveform illustrated here is what appears when only the vibration of the vibrator 102 takes place while no driving signal 110 is supplied to the vibration generating-detecting unit 103.

FIG. 3C shows a signal appearing at a contact A in the wiring changing unit 104. The wiring changing unit 104 is controlled based on a reference signal, or the driving signal 115, supplied from the driving signal generator 107.

In the exemplified structure of the vibrator 102 in the first embodiment shown in FIG. 2, the piezoelectric device 201 is employed as the vibration generating-detecting unit 103, or the electromechanical converting unit, as described above. Strain occurs in the piezoelectric device 201 when a voltage is applied thereto, and vibration 111 is accordingly generated in the piezoelectric device 201 when an AC voltage (the applied driving signal 110) is applied thereto (see FIG. 3A). The fixed end portion 202 of the vibrator 102 is fixed to a support member, and both opposing portions of the vibrator 102 vibrate in opposite directions, respectively, when the piezoelectric device 201 vibrates as indicated by the vibration 111. The opposing portions of the vibrator 102 periodically vibrate in mutually-opposite directions, as indicated by arrows C, respectively. Electric field lines of force 204 are periodically occluded due to the vibration 111 of the vibrator 102, and accordingly, charges are periodically induced in the detecting electrode 101 (see an induced charge signal 116).

In the first embodiment, the wiring changing unit 104 is comprised of an analog switch, for example. A mechanical switch can also be used therefor. The contact A of the wiring changing unit 104 is selectively and alternately connected to the driving signal supplier 105, or an amplifier of the vibration detector 106 for amplifying the vibration detection signal, at given intervals. In the first embodiment, the changing operation is repeated at intervals of a period of the driving signal 115. The manner of the changing operation is not limited thereto. When the periods of vibration generating function and detecting function performed by the vibration generating-detecting unit are respectively equal to a period of the driving signal or integer-multiples of the period of the driving signal 115, these functions can be preferably achieved.

During the time the wiring changing unit 104 is connected to the driving signal supplier 105, the applied driving signal 110 is supplied to the vibration generating-detecting unit 103 through the wiring changing unit 104. During the time the wiring changing unit 104 is connected to the vibration detection signal amplifier, or the vibration detector 106, a detection signal 113 corresponding to the vibration 112 of the vibrator 102 is output to the vibration detector 106 from the vibration generating-detecting unit 103. The detection signal 113 is generated due to the characteristic of the piezoelectric device 201 that it generates a voltage, or the detection signal 113 corresponding to a strain caused in the piezoelectric device by the vibration 112 of the vibrator 102 (see FIG. 3B). The detection signal 113 is converted into an amplified detection signal 114 by the vibration detector 106, which includes the amplifier.

In the driving signal generator 107, the driving signal 115 is generated based on information of the amplified detection signal 114 so that a stable motion of the vibrator 102 can be acquired. Specifically, the driving signal 115 is adjusted so that the amplitude of the vibration of the vibrator 102 is maximized. Alternatively, the driving signal 115 is adjusted so that a phase of the vibration of the vibrator 102 relative to that of the driving signal 115 is set at a desired phase angle (typically, a 90-degree shift of the phase is created) The thus-generated driving signal 115 is transferred to the driving signal supplier 105 to generate the applied driving signal 110.

Upon application of the driving signal with a vibration eigenfrequency of the vibrator 102, vibration with a large amplitude can be obtained by supplying a small amount of energy. This is a resonant condition that can achieve not only a highly-efficient vibration but also a stable vibration. In the resonant condition, sensitivity to the driving signal 115 at a given frequency (about vibration eigenfrequency) is high, and sensitivity to driving signals at other frequencies is low. Further, under the resonant condition, a time constant of a change in the vibration responsive to a change in the frequency of the driving signal 115 is long. Therefore, even when the driving and the vibration are repeated as described above, a resonant vibration can be stably carried out at the frequency of the driving signal 115. At the same time, the detection of the condition of the vibration can also be preferably executed (see FIG. 3C).

When the motion of the vibrator 102 is stabilized, charges are stably induced in a pair of detecting electrodes 101 (a stable generation of the induced charge signal 116). The induced charge signal 116 of charges induced in the detecting electrode 101 is converted into a charge detection signal 117 by the charge detector 108. Since the charge detection signal 117 can also be stably obtained, detection precision of the electric potential measuring apparatus can be improved.

In the above-discussed electric potential measuring apparatus of this embodiment, the period during which the driving signal for generating the mechanical vibration is supplied is different from the period during which the condition of the mechanical vibration is detected. Accordingly, both the supply of the driving signal and the detection of the condition of the vibration can be executed by a single vibration generating-detecting unit. Thus, a stable vibration condition of the vibrator 102 can be always maintained by a relatively simple construction. Consequently, charges can be stably induced in the detecting electrodes 101, and the charge detection signal is stabilized, leading to a very precise electric potential measuring apparatus.

A second embodiment of an electric potential measuring apparatus will be described with reference to FIGS. 4A and 4B. The second embodiment is different from the first embodiment in the construction of the vibration generating-detecting unit 103. As for the rest, the second embodiment is substantially the same as the first embodiment.

In the second embodiment, an electromagnetic actuator is used as the vibration generating-detecting unit 103 (the vibration generator). FIGS. 4A and 4B illustrate two types of vibration generating-detecting units 103, respectively. In FIGS. 4A and 4B, reference numeral 211 designates a vibrator. Reference numeral 212 designates a support frame. Reference numeral 213 designates a torsion bar or spring. Reference numeral 214 designates a pair of pads for the detecting electrodes 101. Reference numeral 215 designates an electric wire. Reference numeral 216 designates a pair of permanent magnets. Reference numeral 217 designates a coil. Reference numeral 218 designates a pad for the coil 217. Reference numeral 219 designates a substrate for supporting the coil 217.

The vibrator 211 is rotatably supported by the torsion bar 213, which is fixed to the support frame 212. The detecting electrodes 101 are arranged on the vibrator 211. The electric wire 215 is disposed on the vibrator 211, the torsion bar 213, and the support frame 212. The pads 214 are disposed on the support frame 212.

Figure 4A:
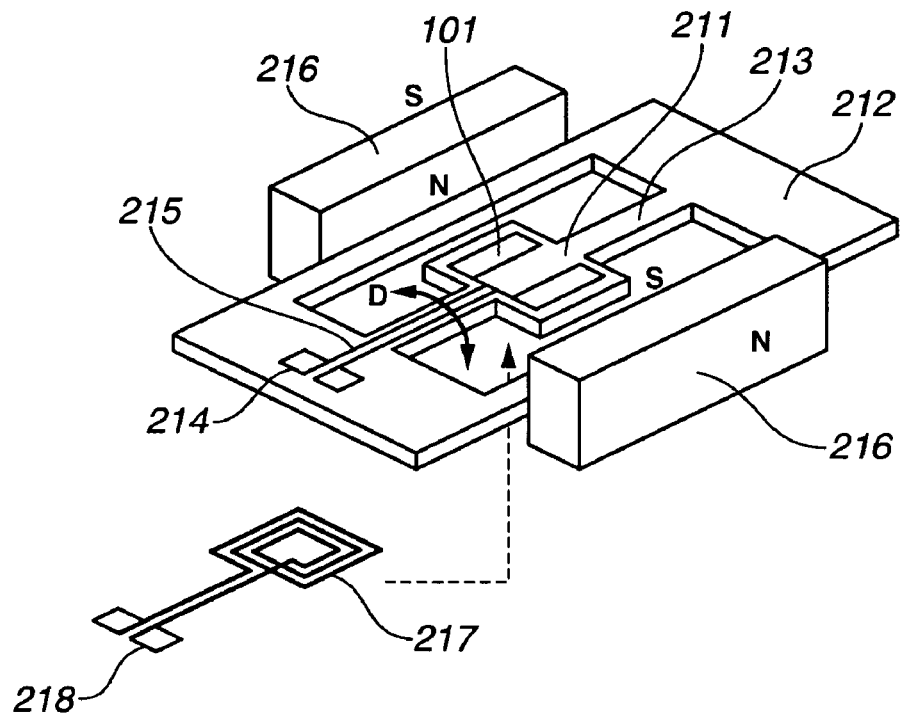
FIGS. 4A and 4B are perspective views illustrating two examples of a vibration generating-detecting unit in an electric potential measuring apparatus of a second embodiment according to the present invention.

In the structure illustrated in FIG. 4A, the coil 217 and the electrode pads 218 are arranged on bottom surfaces of the vibrator 211, the torsion bar 213, and the support frame 212. The magnets 216 are disposed adjacent to both sides of the support frame 212, as illustrated in FIG. 4A. The magnets 216 are magnetized as illustrated in FIG. 4A. This structure is a moving coil type.

Figure 4B:
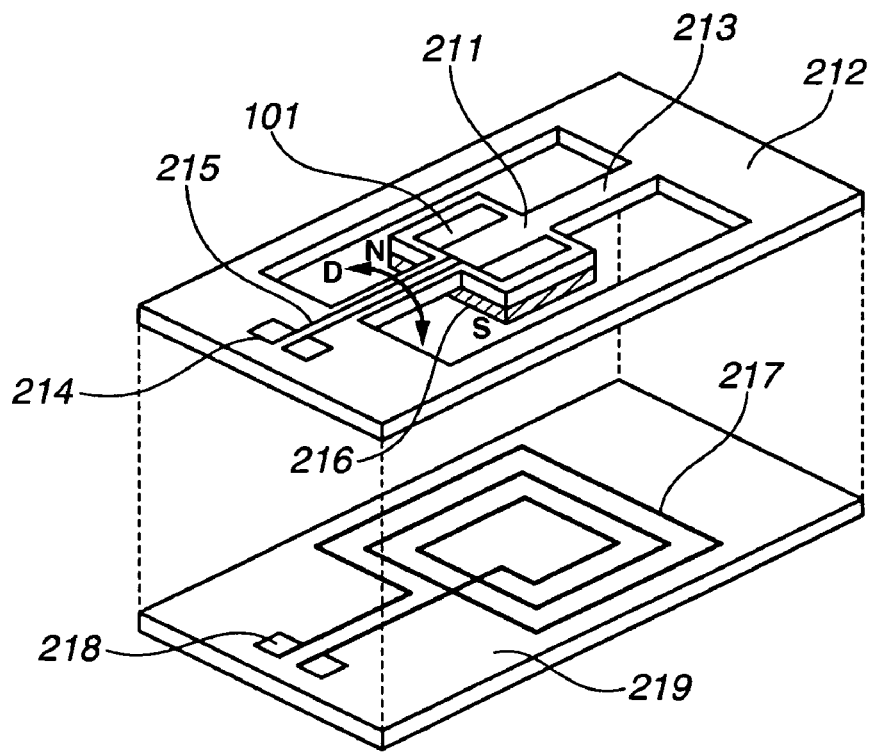

In the structure illustrated in FIG. 4B, the single magnet 216 is arranged on the bottom surface of the vibrator 211. The coil 217 and the coil pads 218 are disposed on the coil substrate 219 as illustrated in FIG. 4B. This structure is a moving magnet type.

When the AC driving signal 110 is supplied to the coil 217, the mechanical vibration of the vibrator 211 is excited about an axis in the extending direction of the torsion bar 213, based on the relationship between the direction of magnetic field of the magnet 216 and the direction of current flow in the coil 217 (Fleming's rule). The vibrator 211 is rotated about the axis of the torsion bars 213 in directions indicated by the arrows D.

During the time when the AC driving signal 110 is not supplied to the coil 217, electromotive force appears in the coil 217 that serves as the vibration generator, based on the relationship between the direction of the vibration of the vibrator 211 and the direction of the magnetic field of the magnet 216. The condition of the vibration of the vibrator 211 can be detected by the detecting circuit 106 that detects the electromotive force appearing in the coil 217.

In the apparatus of this embodiment using such an electromagnetic actuator as the vibration generating-detecting unit, vibration with a large amplitude can be efficiently obtained. Accordingly, a large charge detection signal can be stably obtained with a small-sized structure. Thus, a highly precise electric potential measuring apparatus with a small construction can be achieved according to the second embodiment.

In the structure illustrated in FIG. 4B, there is no need to arrange the magnet close to the vibrator 211 as in the structure illustrated in FIG. 4A. Therefore, according to the structure of FIG. 4B, a very precise electric potential measuring apparatus with a smaller construction can be achieved.

In the above-provided description of the second embodiment, the vibrator 102 is rotated about the torsion bar 213. However, the manner of the mechanical vibration of the vibrator 102 is not limited thereto.

A third embodiment of an electric potential measuring apparatus will be described with reference to FIGS. 5A and 5B, and FIGS. 6A and 6B. The third embodiment is different from the first embodiment in a manner of setting the driving period and the detecting period to be executed by the wiring changing unit 104. As for the rest, the third embodiment is substantially the same as the first or second embodiment.

Figure 5A:
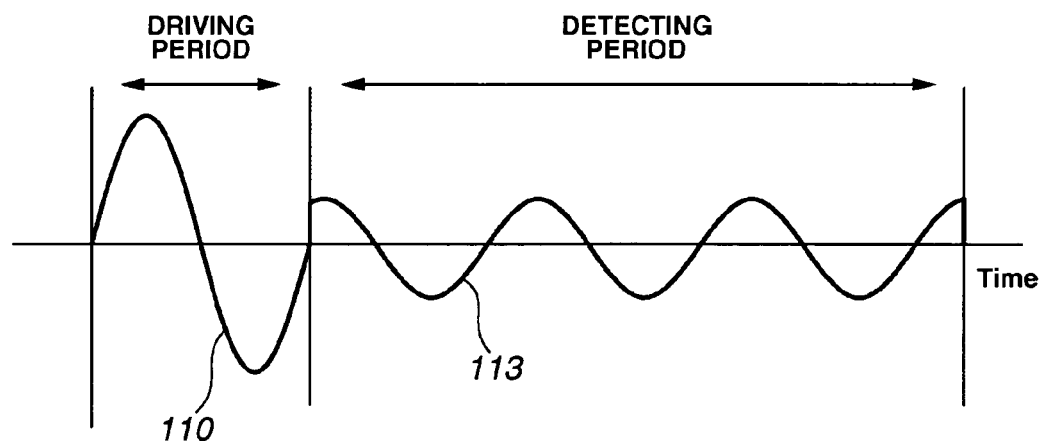
FIGS. 5A and 5B are graphs showing signals appearing in an electric potential measuring apparatus of a third embodiment according to the present invention.
Figure 5B:
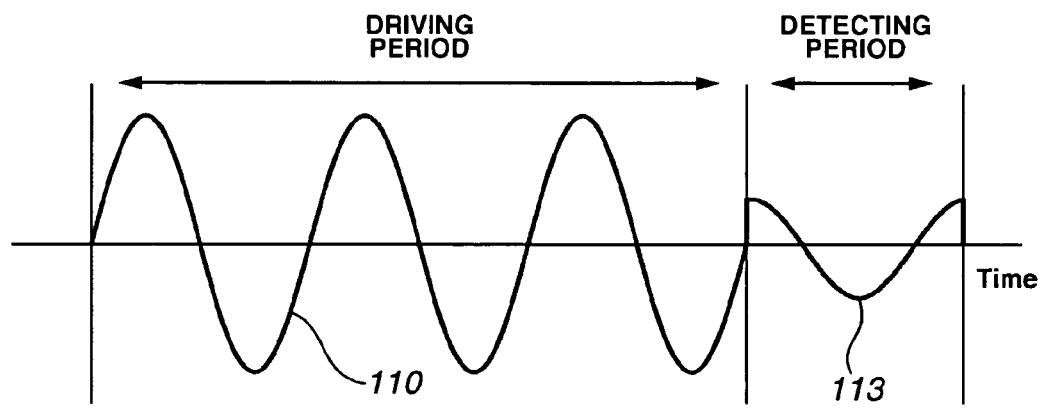

FIGS. 5A and 5B show two types of operations of the wire changing unit 104 in the electric potential measuring apparatus of the third embodiment. The abscissa indicates time, and the ordinate indicates the magnitude of the signal.

In FIG. 5A, the detecting period is set longer than the driving period. Specifically, a ratio between the driving period and the detecting period is set at 1:3. In this construction, the period for detecting the condition of the vibration can be elongated. Accordingly, even when the detection signal 113 of the vibration condition is small, the condition of the vibration can be accurately detected.

In FIG. 5B, the detecting period is set shorter than the driving period. Specifically, a ratio between the driving period and the detecting period is set at 3:1. In this construction, the period for supplying the driving signal 110 to the vibration generating-detecting unit 103 is increased. Accordingly, the driving signal 110 supplied during the driving period can be decreased. Further, even when a large driving signal is required, a stable driving signal can be supplied since a load on the driving signal supplier 105 is lightened. Thus, even when the driving signal 110 is large, a stable vibration of the vibrator 102 can be achieved.

Figure 6A:
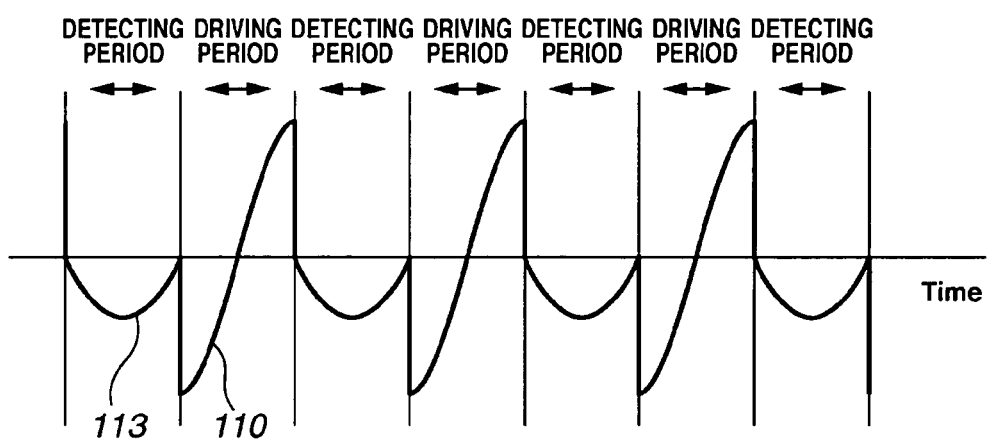
FIGS. 6A and 6B are graphs showing signals appearing in the third embodiment.
Figure 6B:
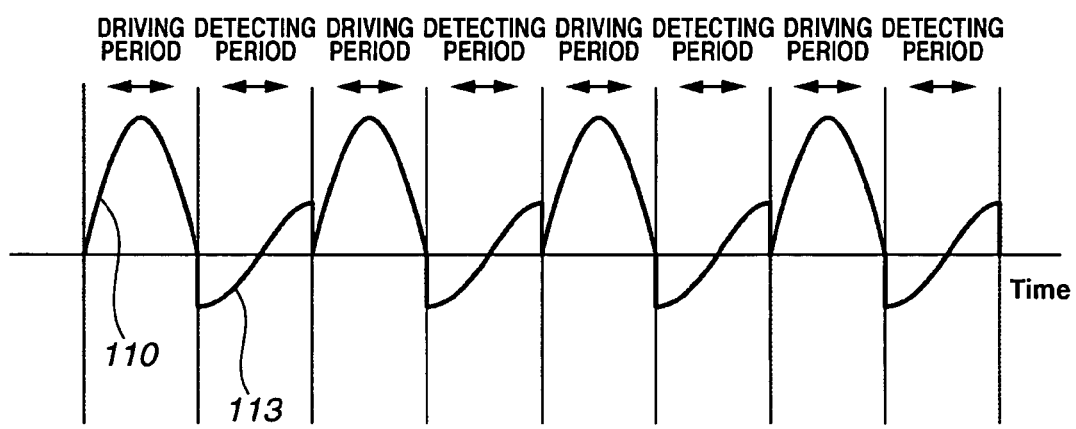

In the constructions of FIGS. 6A and 6B, the driving period and the detecting period are not equal to a period or its integer-multiples of the driving signal for the vibrator 102, respectively. The sum of the driving period and the detecting period, however, is equal to a period or its integer-multiples of the driving signal for the vibrator 102. Here, the sum is equal to a period of the driving signal.

In the construction of FIG. 6A, the detecting period is set so that a peak portion of the detection signal can be detected. Hence, the maximum of the vibration can be always monitored. Further, the driving period can be set such that energy can be efficiently supplied to vibrator 102.

In the construction of FIG. 6B, the detecting period is set so that a zero-crossing point of the detection signal can be detected. Accordingly, the phase timing of the vibration can be always monitored. Further, the driving period can be set such that energy can be efficiently supplied to vibrator 102.

When either of the above-discussed constructions is adopted, the driving period can be set as long as possible under a given limited condition, while the condition of the vibration is detected. Therefore, driving the vibrator 211 can be efficiently performed, and a stable vibration of the vibrator 211 can also be achieved.

In the electric potential measuring apparatus according to this embodiment, a stable vibration can be obtained by an appropriate setting of the ratio between the driving period and the detecting period. Thus, a very precise electric potential measuring apparatus can be achieved.

A fourth embodiment of an electric potential measuring apparatus will be described with reference to FIGS. 7A to 7C, FIGS. 8A and 8B, and FIGS. 9A and 9B. The fourth embodiment is different from the above embodiments in the charge detector 108 for detecting charges induced in the detecting electrode 101. As for the rest, this embodiment is the same as any one of the first to third embodiments.

Figure 7A:
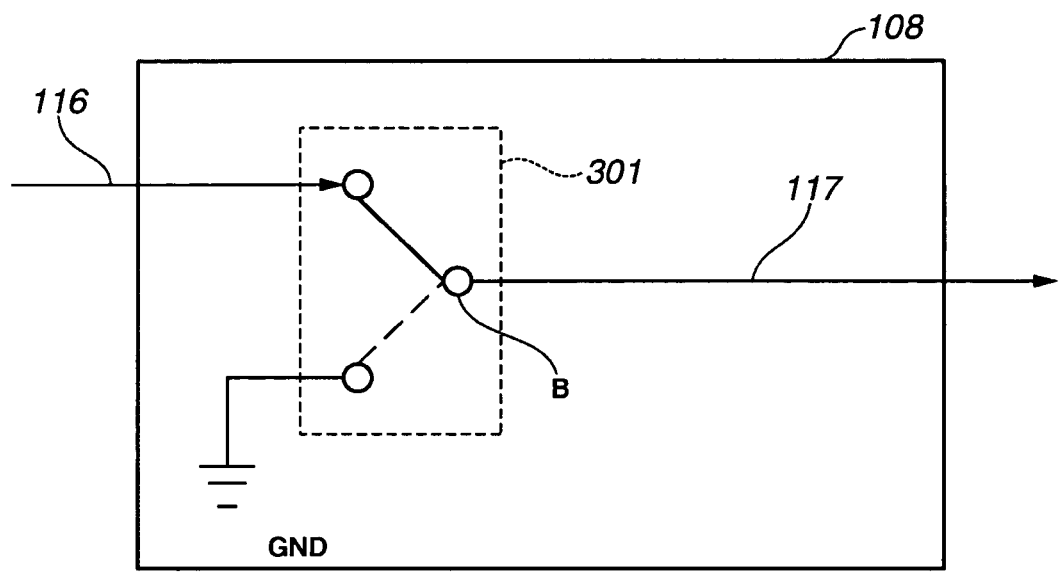
FIGS. 7A to 7C are schematic block diagrams illustrating three examples of a charge detector in an electric potential measuring apparatus of a fourth embodiment according to the present invention.
Figure 7B:
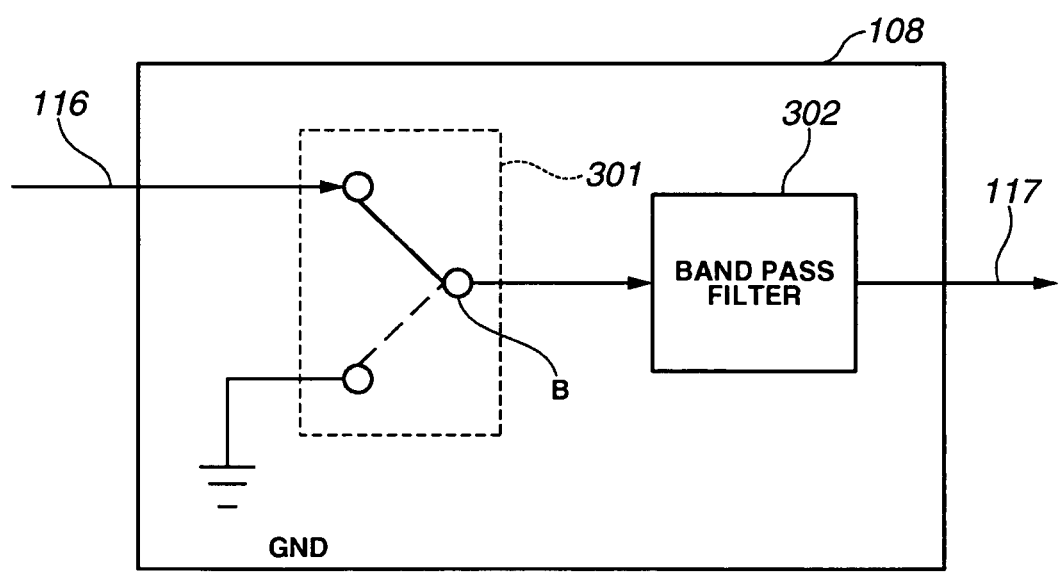
Figure 7C:
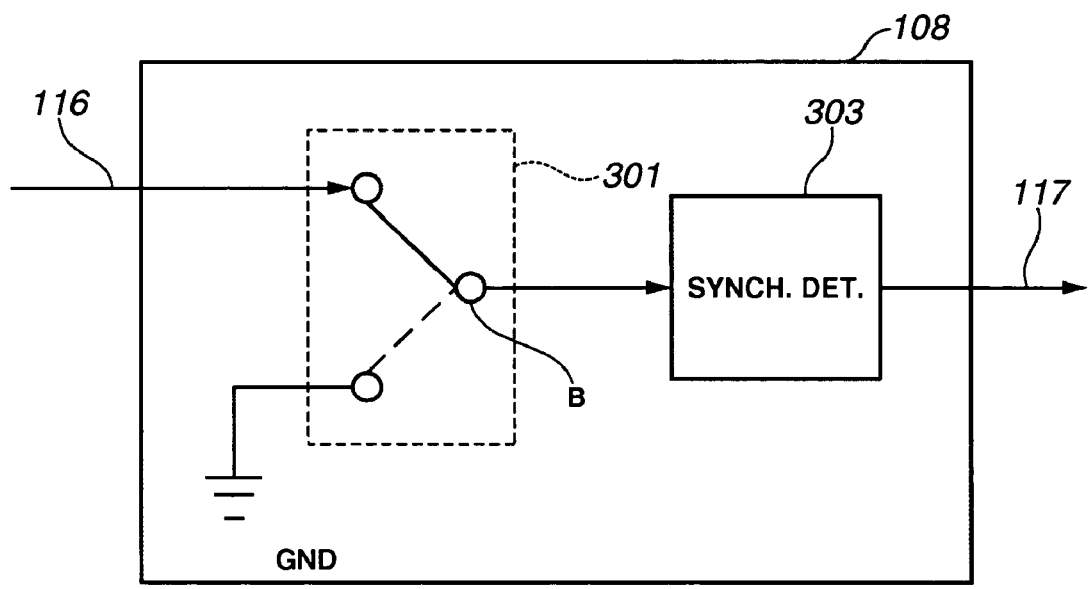

FIGS. 7A to 7C illustrate three types of the charge detectors 108 used in the fourth embodiment of this invention, respectively. In those figures, reference numeral 301 designates an analog switch, reference numeral 302 designates a band pass filter, and reference numeral 303 designates a synchronous detector. FIGS. 8A and 8B, and FIGS. 9A and 9B show signals appearing in the charge detector 108 in the apparatus of this embodiment, respectively. The abscissa indicates time, and the ordinate indicates the magnitude of the signal. In the following description of the fourth embodiment, the same driving period and detecting period as those shown in FIG. 3C are used. However, the driving period and the detecting period are not limited thereto in the fourth embodiment.

In the structure of FIG. 7A, the charge detector 108 includes the analog switch 301. A contact B is connected to the ground (GND) during the driving period, and to the detecting electrode 101 during the detecting period. In an ordinary electric potential measuring apparatus, a signal (noise) other than the signal of charges induced in the detecting electrode 101 by the photosensitive drum (the measurement object) is generated by the driving signal 110. This noise becomes an adverse factor that reduces the detecting resolution when a very precise measurement of the electric potential is required.

Figure 8A:
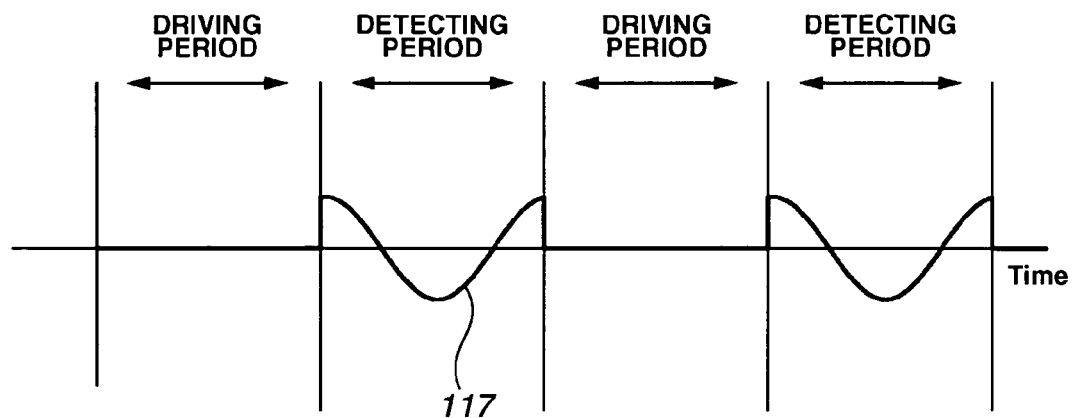
FIGS. 8A and 8B are graphs showing signals appearing in a charge detector in the fourth embodiment.

In the structure in which the charge detector 108 as illustrated in FIG. 7A is used, no detection of the induced charges is conducted during the driving period for supplying the driving signal 110. In other words, the period when the signal is output from the charge detector 108 is within the period when the vibration generating-detecting unit 103 performs the detecting function. Accordingly, the noise due to the driving signal 110 does not influence in the charge detection signal 117. FIG. 8A shows the charge detection signal 117 in this case. It is thus possible to perform the measurement of the electric potential without any influence of the noise due to the driving signal 110.

Figure 8B:
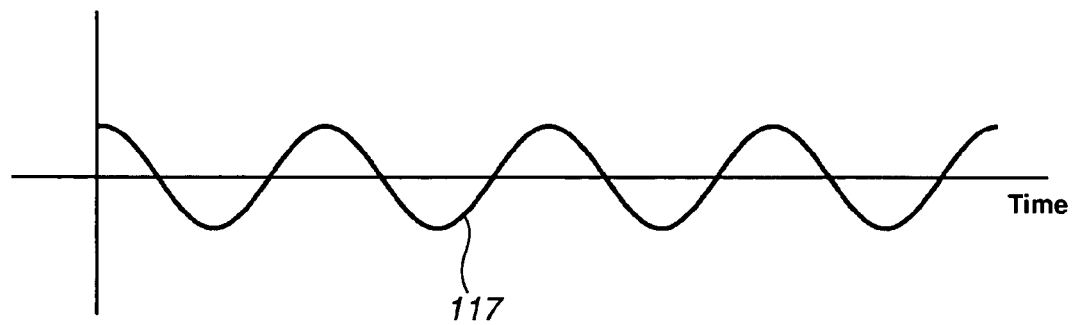

FIG. 7B illustrates the structure in which the band pass filter 302 is added to the structure of FIG. 7A. A central frequency of the band pass filter 302 is set close to the driving frequency of the vibrator 102. Separate fragmentary charge detection signals 117 as illustrated in FIG. 8A can be hence converted into a continuous signal 117 as illustrated in FIG. 8B. Thus, the charge detection signal 117 can be readily processed at the later stage. Further, components at frequencies remote from the vibration frequency can be removed, so that almost no noise at other frequencies in the charge detection signal 117 is detected.

Figure 9A:
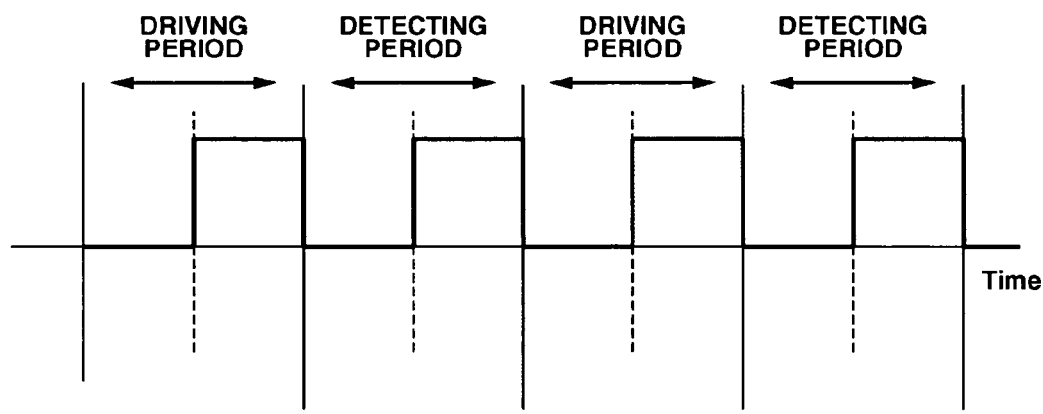
FIGS. 9A and 9B are graphs showing signals appearing in the charge detector in the fourth embodiment.

FIG. 7C illustrates the structure in which the charge detector 108 includes the synchronous detecting circuit 303 as well as the structure illustrated in FIG. 7A. The synchronous detection is executed by using a synchronous signal (its duty is 50%) that is synchronous with the driving period of the vibrator 102 as illustrated in FIG. 9A. Accordingly, it becomes easy to pick up only the charge detection signal 117 near the driving frequency of the vibrator 102.

Further, it is more preferable that the driving period and the detecting period are equal to a period or its integer-multiples of the vibration period of the vibrator 102, respectively. In such a case, no error appears in the value of a detected signal even when the phase of the charge detector 108 shifts. Thus, a more accurate value can be detected.

Figure 9B:
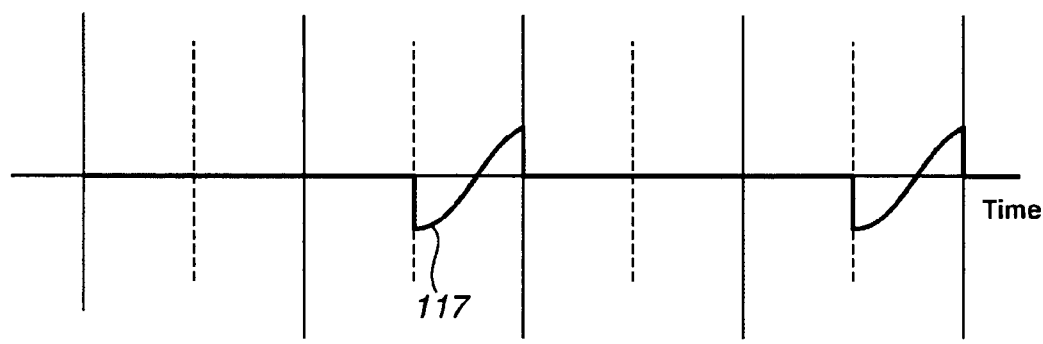

It is further possible to adopt another structure where the charge detector 108 includes an analog switch 301, similar to the structure illustrated in FIG. 7A. In this structure, the analog switch 301 operates differently from the above-provide description of the structure of FIG. 7A. Here, the contact B in the analog switch 301 is connected to the ground (GND) during the driving-period. During the detecting period, the contact B is connected to the detecting electrode 110 when the synchronous signal is HIGH, while connected to GND when the synchronous signal is LOW. Specifically, the charge detection signal 117 obtained in this case is as illustrated in FIG. 9B. In such a structure, both the exchange between the driving period and the detecting period and very precise synchronous detection can be achieved with a simple construction.

In the electric potential measuring apparatus of the fourth embodiment using the above-discussed charge detector 108, charges induced in the detecting electrode 110 can be detected under a condition in which the influence of the noise due to the driving signal is reduced. Accordingly, it is possible according to the fourth embodiment to provide a highly precise electric potential measuring apparatus in which the adverse influence of the driving signal is reduced.

Figure 10:
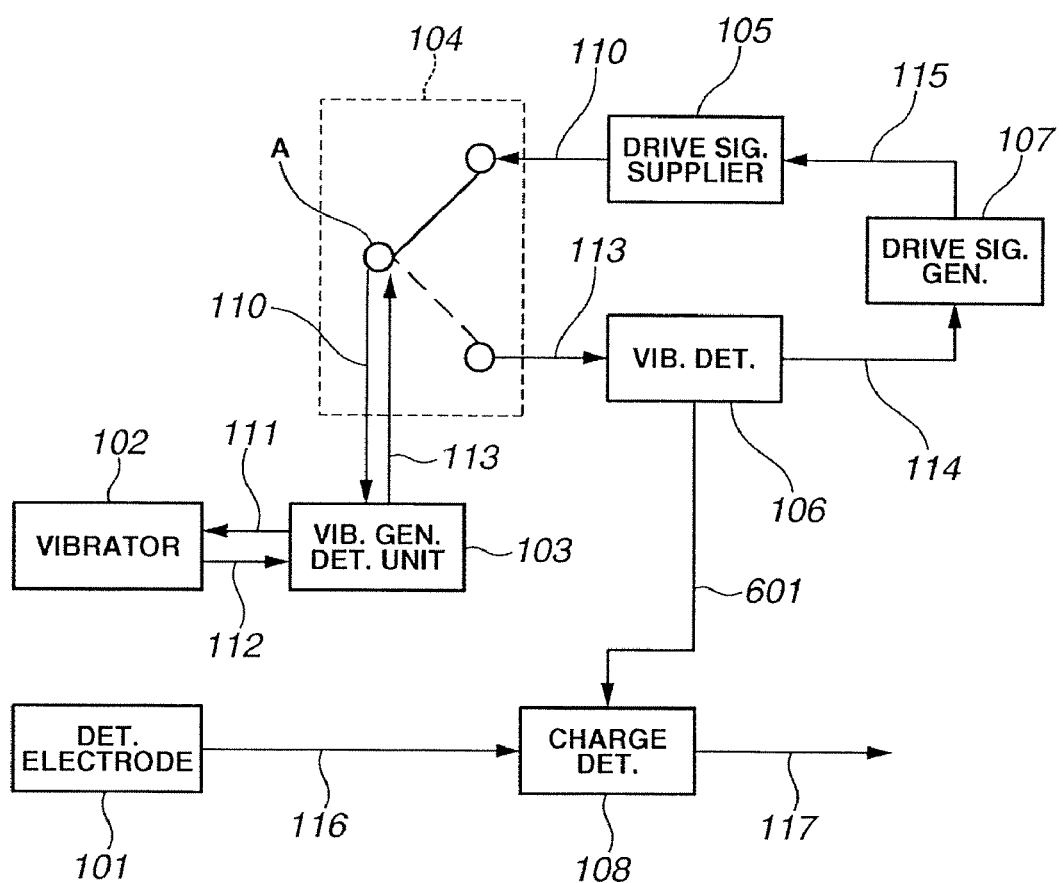
FIG. 10 is a block diagram illustrating an electric potential measuring apparatus of a fifth embodiment according to the present invention.

A fifth embodiment of an electric potential measuring apparatus will be described with reference to FIG. 10. The fifth embodiment is different from the first embodiment in that an amplified detection signal 601 from the amplifier of the detector 106 for amplifying the vibration detection signal is supplied to the charge detector 108. As for the rest, the fifth embodiment is substantially the same as the embodiment shown in FIG. 1.

In the fifth embodiment, an arithmetic operation of the induced charge signal 116 and the amplified detection signal 601 is conducted in the charge detector 108 to obtain the charge detection signal 117. Specifically, the arithmetic operation is carried out by dividing the induced charge signal 116 by the amplified detection signal 601 that shows the magnitude of the vibration of the vibrator 102. Thus, the charge detection signal 117 is obtained. Even when the vibration of the vibrator 102 varies, the charge detection signal 117 can be precisely obtained by that arithmetic processing.

For example, when the vibration of the vibrator 102 varies due to variation in the resonant frequency by thermal phenomenon, the induced charge signal 116 changes in proportion to the magnitude of the vibration of the vibrator 102 even if there is no change in the electric potential of the measurement object (not shown). As a result, a value different from an actual electric potential of the measurement object is detected. Also in such a case, the charge detection signal 117 can be corrected to an accurate magnitude by the above-described structure.

Thus, in the fifth embodiment, the electric potential can be measured with higher precision. Further, very precise measurement can be achieved unless the vibrator 102 is very precisely controlled to have a predetermined amplitude. Therefore, a very precise measurement of the electric potential can be attained even when control precision of the amplitude of the vibrator 102 by the driving signal generator 107 is low, or controllability of the vibrator 102 is low. Consequently, highly precise measurement of the electric potential can be achieved by a simpler construction.

Further, highly precise measurement of the electric potential can be achieved even when the driving signal supplied from the driving signal generator 107 is fixedly set at a predetermined waveform without using the amplified detection signal 114. Accordingly, the driving signal generator 107 can be formed with a very simple structure.

In the foregoing, a description is given mainly for electric potential measuring apparatuses or methods, but the present invention can be applied to other apparatuses or methods. The present invention can be applied to electrostatic capacitance measuring apparatuses or methods with substantially the same construction. For example, the present invention can be applied to an apparatus in which an electric potential of the measurement object 203, 401 or 501 is maintained at a certain constant magnitude, and a change in the electrostatic capacitance between the measurement object 203, 401 or 501 and the detecting electrode 101 or 502 is detected. In such an electrostatic capacitance measuring apparatus or method of the present invention, a change in the distance between the measurement object and the electrode, a change in the dielectric constant of a portion between the measurement object and the electrode, or the like can be measured by detection of a change in the electrostatic capacitance.

A description will now be given for an image forming apparatus of a sixth embodiment using an electric potential measuring apparatus of the present invention, with reference to FIG. 11. The electric potential measuring apparatus can be any one of the above-described first to fifth embodiments.

Figure 11:
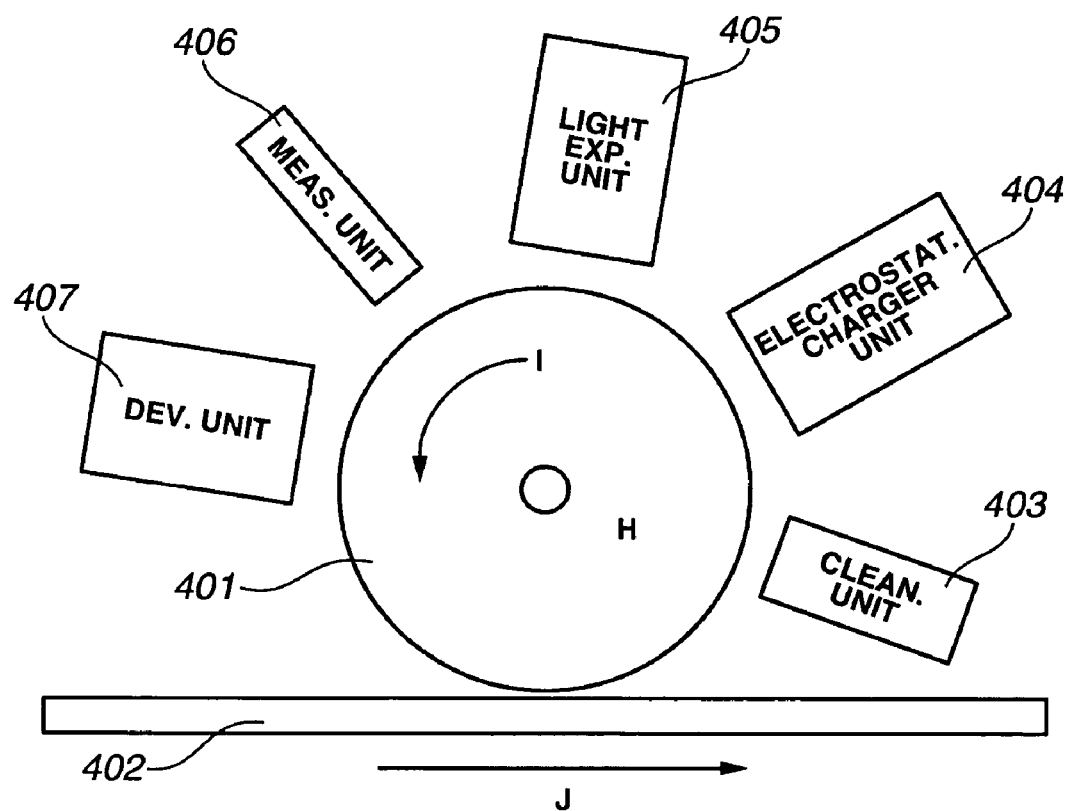
FIG. 11 is a view, taken along a plane perpendicular to a rotation axis of a photosensitive drum, schematically illustrating constituent units in an image forming apparatus of a sixth embodiment according to the present invention.
Figure 12:
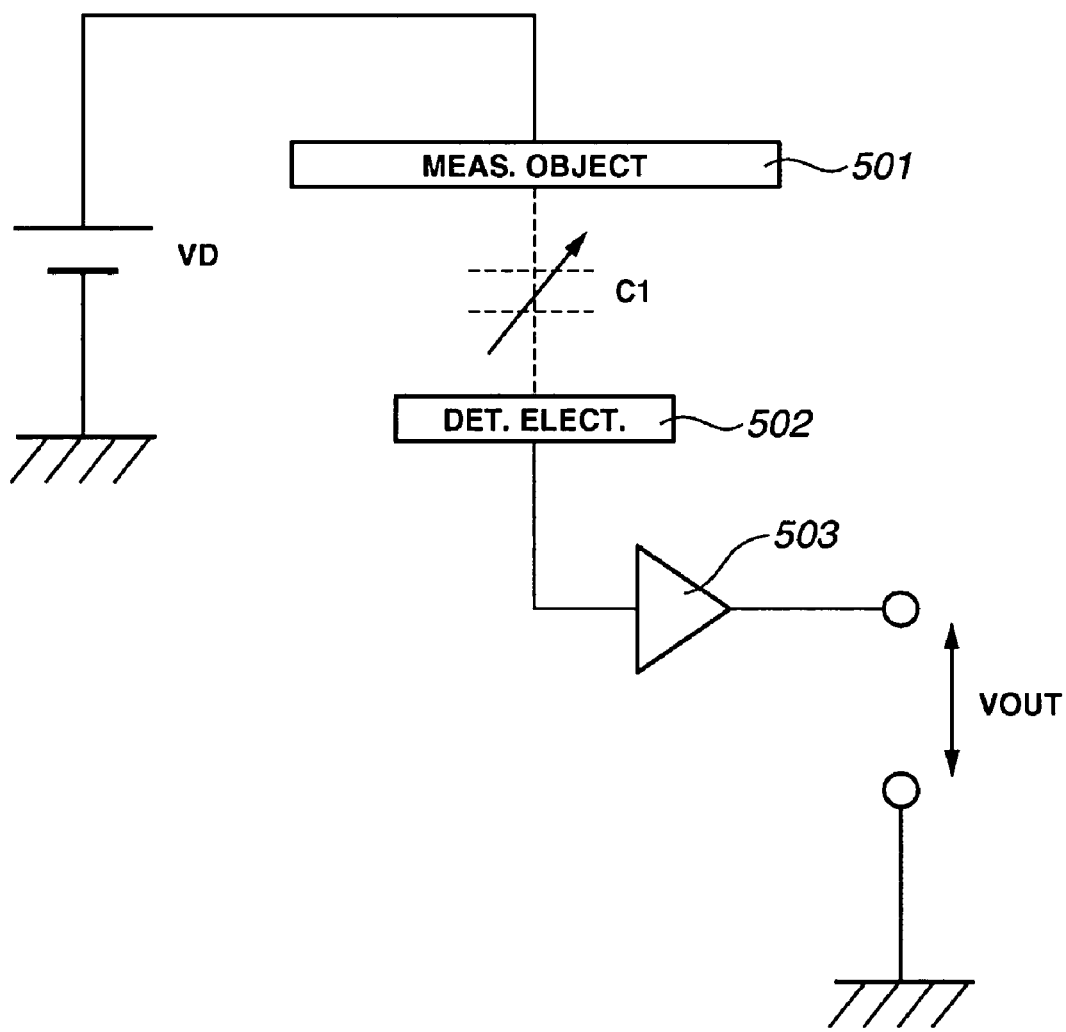
FIG. 12 is a view schematically illustrating an ordinary non-contacting electric potential measuring apparatus in which the electric potential of a measurement object is measured without contact with the measurement object.

FIG. 11 is a schematic view, taken along a plane perpendicular to a rotation axis H of a photosensitive drum (a measurement object) 401, illustrating the arrangement of the following units around the drum 401. In FIG. 11, reference numeral 402 designates a transferring material (e.g., a sheet of paper) sandwiched between a transferring material conveying roller (not shown) and the photosensitive drum 401. Reference numeral 403 designates a cleaner unit. Reference numeral 404 designates an electrostatic charging unit. Reference numeral 405 designates a light exposing unit. Reference numeral 406 designates an electric potential measuring unit of the present invention. Reference numeral 407 designates a developing unit. An image forming unit is comprised of the photosensitive drum 401, the electrostatic charging unit 404, the light exposing unit 405, and the like.

The photosensitive drum 401 rotates in a direction I about the rotation axis H. The photosensitive drum 401 is charged by the electrostatic charging unit 404, and exposed to light by the light exposing unit 405. A charged pattern is thus formed on the photosensitive drum 401. The electric potential measuring unit 406 measures the electric potential of the charged pattern on the photosensitive drum 401. At the developing unit 407, toner or the like is attached only to the charged pattern (or a portion other than the charged portion) to achieve the development. An image is then transferred to the paper 402 moving in a direction J. After that, the photosensitive drum 401 is cleaned by the cleaner unit 403.

In the above-described structure, the electrostatic charging unit 404, the light exposing unit 405 and the like are controlled based on the measurement result obtained by the electric potential unit 406, and the image formation is regulated. In the image forming apparatus, there is a possibility that the photosensitive drum 401 may have an eccentricity, the electrostatic charging unit 404 may create a difference in the charged level, the photosensitive drum 401 may have an individual different surface condition, and changes may occur in the units with time. Therefore, the electric potential of the charged pattern formed on the photosensitive drum 401 may vary depending on the individual image forming apparatus, or with the lapse of time. The variation in the electric potential can result in a difference in the image density on the paper 402 when the image is formed by the image forming apparatus. Thus, the difference in the magnitude of the charged pattern on the photosensitive drum 401 can influence the quality of the image formed by the image forming apparatus.

The foregoing embodiment of the electric potential measuring apparatus can be employed in the image forming apparatus as above-described. The electric potential measuring apparatus of the present invention has a relatively simple construction, and can perform very precise measurement of the electric potential. Therefore, a high-quality image is ensured when the charging unit 404, the exposing unit 405, and so forth are controlled based on the measurement result obtained by such an electric potential measuring apparatus. The control of the electrostatic charging unit 404, the light exposing unit 405, and so forth, i.e., setting of the condition of the image formation, can be performed by regulating the electrostatic charging voltage of the charging unit 404, or changing the amount of light or the light radiation time of the light exposing unit 405, for example. According to the sixth embodiment, an image forming apparatus capable of forming a high-quality image can be achieved.

As described in the foregoing, in electric potential or electrostatic capacity measuring apparatuses and methods of the present invention, generation of the vibration and detection of the condition of the vibration can be executed by a simple unit, such as a vibration generating-detecting unit. Therefore, relatively stable vibration can be achieved without increasing the number of components of the apparatus. Consequently, it is possible to provide a relatively high-performance electric potential or electrostatic capacity measuring apparatus and method capable of obtaining a stable output.

Except as otherwise disclosed herein, the various components shown in outline or in block form in the figures are individually well-known and their internal construction and operation are not critical either to the making or using of the present invention or to a description of the best mode of the invention.

While the present invention has been described with respect to what is presently considered to be the embodiments and examples, it is to be understood that the invention is not limited to the disclosed embodiments and examples. The present invention is intended to cover various modifications and equivalent arrangements included within the spirit and the scope of the appended claims.

This application claims priority from Japanese Patent Application Nos. 2005-235586, filed Aug. 16, 2005, and 2006-178885, filed Jun. 29, 2006, the contents of which are hereby incorporated by reference.

What is claimed is:

1. An electric potential measuring apparatus operable to measure an electric potential of a measurement object, the electric potential measuring apparatus comprising:

a detecting electrode;

a modulator for changing an electrostatic capacitance between the measurement object and the detecting electrode by mechanical vibration of the modulator, wherein the modulator is stably driven about an eigenfrequency of the modulator;

a charge detector for detecting an amount of charges electrostatically induced in the detecting electrode by the modulator;

a vibration generator for exciting the mechanical vibration; and a detector for detecting a condition of the mechanical vibration from a condition of the vibration generator, a switching unit coupled to the vibration generator and the detector, whereby one of the excitement of the mechanical vibration and detection of the condition of the mechanical vibration is selectively and alternately performed.

2. An electric potential measuring apparatus according to claim 1, wherein the vibration generator includes a piezoelectric device.

3. An electric potential measuring apparatus according to claim 1, wherein the vibration generator includes an electromagnetic actuator.

4. An electric potential measuring apparatus according to claim 1, wherein the vibration generator includes an electromechanical actuator.

5. An electric potential measuring apparatus according to claim 1, wherein the switching unit alternately couples to one of the vibration generator and the detector for detecting the condition of the mechanical vibration during a vibration period and a detecting period, respectively,
   wherein a sum of a driving period for exciting the mechanical vibration and a detecting period for detecting the condition of the mechanical vibration is equal either to a period of the mechanical vibration, or integer-multiples of the period of the mechanical vibration.

6. An electric potential measuring apparatus according to claim 1,
   wherein the charge detector includes an output for outputting a charge signal;
   wherein a period for outputting a signal from the charge detector is within a period for detecting the condition of the mechanical vibration from the condition of the vibration generator.

7. An electric potential measuring apparatus according to claim 1, wherein the charge detector includes a band pass filter with a central frequency close to a frequency of the mechanical vibration.

8. An electric potential measuring apparatus according to claim 1, wherein the charge detector includes synchronous detecting circuit using a period of the mechanical vibration.

9. An image forming apparatus comprising:
   the electric potential measuring apparatus according to claim 1; and
   an image forming unit,
   wherein the electric potential measuring apparatus includes a face, on which the detecting electrode is disposed, is arranged facing a face of the measurement object of the image forming unit, and wherein the image forming unit controls image formation, based on a signal detected by the electric potential measuring apparatus.

10. An electric potential measuring apparatus according to claim 1,
    wherein the selective performance of the excitement of the mechanical vibration and the detection of the condition of the mechanical vibration, are alternately performed at a periodic interval.

11. An electric potential measuring apparatus according to claim 1, wherein the switching unit selectively and alternately couples to one of the vibration generator for exciting the mechanical vibration and the detector for detecting the condition of the mechanical vibration during a vibration period and a detecting period, respectively.

12. An electric potential measuring method comprising the steps of:
    changing an electrostatic capacitance between a measurement object and a detecting electrode by mechanical vibration of the modulator, wherein the modulator is stably driven about an eigenfrequency of the modulator;
    detecting an amount of charges electrostatically induced in the detecting electrode in the changing step; and
    measuring an electric potential of the measurement object based on a result obtained in the detecting step, wherein a condition of the mechanical vibration is detected, a manner of excitement of the mechanical vibration is controlled based on a result of the detection of the condition of the mechanical vibration, and a period for exciting the mechanical vibration and a period for detecting the condition of the mechanical vibration are set so that those periods do not overlap with each other.

13. An electrostatic capacitance measuring method comprising the steps of:
    changing an electrostatic capacitance between a measurement object and a detecting electrode by mechanical vibration of the modulator, wherein the modulator is stably driven about an eigenfrequency of the modulator;
    detecting an amount of charges electrostatically induced in the detecting electrode in the changing step; and
    measuring the electrostatic capacitance between the measurement object and the detecting electrode based on a result obtained in the detecting step, wherein the condition of the mechanical vibration is detected, a manner of excitement of the mechanical vibration is controlled based on a result of the detection of the condition of the mechanical vibration, and a period for exciting the mechanical vibration and a period for detecting the condition of the mechanical vibration are set so that those periods do not overlap with each other.

14. An electric potential measuring apparatus operable to measure an electric potential of a measurement object, the electric potential measuring apparatus comprising:
    a detecting electrode;
    a modulator for changing an electrostatic capacitance between the measurement object and the detecting electrode by mechanical vibration;
    a charge detector for detecting an amount of charges electrostatically induced in the detecting electrode by the modulator;
    a vibration generator for exciting the mechanical vibration; and
    a detector for detecting a condition of the mechanical vibration from a condition of the vibration generator, wherein the vibration generator comprises the detector for detecting a condition of the mechanical vibration, and
    a switching unit coupled to the vibration generator that comprises the detector, whereby one of the excitement of the mechanical vibration and detection of the condition of the mechanical vibration is selectively and alternately performed the vibration generator that comprises the detector.

15. An electric potential measuring apparatus according to claim 14,
    wherein the switching unit selectively and alternately couples to one of the vibration generator for exciting the mechanical vibration and the detector for detecting the condition of the mechanical vibration during a vibration period and a detecting period, respectively.

16. An electric potential measuring apparatus according to claim 14,
    wherein the selective performance of the excitement of the mechanical vibration and the detection of the condition of the mechanical vibration, are alternately performed at a periodic interval.

17. An electrostatic capacitance measuring apparatus comprising:
a detecting electrode;
a modulator for changing an electrostatic capacitance between a measurement object and the detecting electrode by mechanical vibration of the modulator, wherein the modulator is stably driven about an eigenfrequency of the modulator;
a charge detector for detecting the amount of charges electrostatically induced in the detecting electrode by the modulator; and
a vibration generating-detecting unit for selectively performing one of excitement of the mechanical vibration and detection of the condition of the mechanical vibration; and
a switching unit coupled to the vibration generating-detecting unit, whereby one of the excitement of the mechanical vibration and detection of the condition of the mechanical vibration is selectively and alternately performed.

18. An image forming apparatus comprising: the electrostatic capacitance measuring apparatus according to claim 17; and an image forming unit,
wherein the electrostatic capacitance measuring apparatus includes a face, on which the detecting electrode is disposed, is arranged facing a face of the measurement object of the image forming unit, and wherein the image forming unit controls image formation, based on a signal detected by the electrostatic capacitance measuring apparatus.

* * * * *

UNITED STATES PATENT AND TRADEMARK OFFICE
CERTIFICATE OF CORRECTION

PATENT NO. : 7,372,278 B2
APPLICATION NO. : 11/500926
DATED : May 13, 2008
INVENTOR(S) : Atsushi Kandori et al.

It is certified that error appears in the above-identified patent and that said Letters Patent is hereby corrected as shown below:

TITLE PAGE ITEM [54] TITLE
    Line 2, "APPARATUS ELECTROSTATIC" should read --APPARATUS, ELECTROSTATIC--.

COLUMN 1
    Line 2, "APPARATUS ELECTROSTATIC" should read --APPARATUS, ELECTROSTATIC--.
    Line 48, "electrode 502 are" should read --electrode 502 is--.

COLUMN 6
    Line 28, "created)" should read --created).--.

COLUMN 8
    Line 53, "vibrator" should read --the vibrator--.

COLUMN 9
    Line 37, "in" should be deleted.

COLUMN 10
    Line 5, "provide" should read --provided--.
    Line 7, "driving-period." should read --driving period.--.

COLUMN 13
    Line 2, "detector, whereby" should read --detector, ¶whereby--.
    Line 16, "claim 1, wherein" should read --claim 1, ¶wherein--.
    Line 39, "synchronous" should read --a synchronous--.
    Line 47, "is" should be deleted.

COLUMN 14
    Line 55, "performed" should read --performed by--.

UNITED STATES PATENT AND TRADEMARK OFFICE
CERTIFICATE OF CORRECTION

PATENT NO. : 7,372,278 B2
APPLICATION NO. : 11/500926
DATED : May 13, 2008
INVENTOR(S) : Atsushi Kandori et al.

It is certified that error appears in the above-identified patent and that said Letters Patent is hereby corrected as shown below:

COLUMN 16
      Line 11, "is" should be deleted.

Signed and Sealed this

Eleventh Day of November, 2008

JON W. DUDAS
*Director of the United States Patent and Trademark Office*